(12) United States Patent  (10) Patent No.: US 8,460,345 B2
Steger et al.  (45) Date of Patent: Jun. 11, 2013

(54) METHOD AND APPARATUS FOR BONE FRACTURE FIXATION

(75) Inventors: Shon D. Steger, Jacksonville, FL (US); Brian S. Schumacher, Orlando, FL (US); Jeffrey A. Duncan, Jacksonville, FL (US)

(73) Assignee: Biomet Microfixation, LLC, Warsaw, IN (US)

( * ) Notice: Subject to any disclaimer, the term of this patent is extended or adjusted under 35 U.S.C. 154(b) by 703 days.

(21) Appl. No.: 12/732,009

(22) Filed: Mar. 25, 2010

(65) Prior Publication Data

US 2010/0179600 A1  Jul. 15, 2010

Related U.S. Application Data

(63) Continuation of application No. 10/980,705, filed on Nov. 3, 2004, now abandoned, which is a continuation-in-part of application No. 10/081,166, filed on Feb. 22, 2002, now Pat. No. 7,052,499.

(51) Int. Cl.
*A61B 17/80* (2006.01)

(52) U.S. Cl.
USPC .......................................... 606/280; 606/285

(58) Field of Classification Search
USPC .............................. 606/60, 280, 70, 281–285
See application file for complete search history.

(56) References Cited

U.S. PATENT DOCUMENTS

| | | | |
|---|---|---|---|
| 1,105,105 A | 7/1914 | Sherman | |
| 2,489,870 A | 11/1949 | Dzus | |
| 2,494,229 A | 1/1950 | Collison | |
| 2,631,584 A | 3/1953 | Purificato | |
| 3,488,779 A | 1/1970 | Christensen | |
| 4,219,015 A | 8/1980 | Steinemann | |
| 4,429,690 A | 2/1984 | Angelino-Pievani | |
| 4,484,570 A | 11/1984 | Sutter et al. | |
| 4,683,878 A | 8/1987 | Carter | |
| 4,708,132 A | 11/1987 | Silvestrini | |
| 4,903,691 A | 2/1990 | Heinl | |
| 4,905,679 A | 3/1990 | Morgan | |
| 4,959,065 A | 9/1990 | Arnett et al. | |
| 4,973,332 A | 11/1990 | Kummer | |
| 5,108,395 A | 4/1992 | Laurain | |
| 5,108,399 A | 4/1992 | Eitenmuller et al. | |

(Continued)

FOREIGN PATENT DOCUMENTS

| DE | 867422 C | 2/1953 |
|---|---|---|
| FR | 2556583 A1 | 6/1985 |
| GB | 2324470 A | 10/1998 |

OTHER PUBLICATIONS

Casha, A.R. et al., A Biomechanical Study of Median Sternotomy Closure Techniques, European Journal of Cardio-thoracic Surgery 15, 1999, pp. 365-369.

(Continued)

*Primary Examiner* — Andrew Yang
(74) *Attorney, Agent, or Firm* — Harness, Dickey

(57) ABSTRACT

A method according to the present disclosure may include determining a load to be supported across separated bone regions by a bridge region of a bone plate. The method may further include determining an acceptable cut force (CF) for the bridge region, determining a cross-sectional area (a) of the bridge region based on the determined load, and determining a height (h) and a width (w) of the bridge region. A bone plate may be provided including a bridge region having the height (h) and width (w) for securing the separated bone regions.

20 Claims, 12 Drawing Sheets

U.S. PATENT DOCUMENTS

| | | |
|---|---|---|
| 5,129,899 A | 7/1992 | Small et al. |
| 5,139,498 A | 8/1992 | Astudillo Ley |
| 5,147,363 A | 9/1992 | Harle |
| 5,151,103 A | 9/1992 | Tepic et al. |
| 5,180,381 A | 1/1993 | Aust et al. |
| 5,180,382 A | 1/1993 | Frigg et al. |
| 5,269,784 A | 12/1993 | Mast |
| 5,303,718 A | 4/1994 | Krajicek |
| 5,336,224 A | 8/1994 | Selman |
| 5,358,367 A | 10/1994 | Yang |
| 5,372,598 A | 12/1994 | Luhr et al. |
| 5,403,136 A | 4/1995 | Mathys |
| 5,413,577 A | 5/1995 | Pollock |
| 5,468,242 A | 11/1995 | Reisberg |
| 5,474,551 A | 12/1995 | Finn et al. |
| 5,474,553 A | 12/1995 | Baumgart |
| 5,505,731 A | 4/1996 | Tornier |
| 5,520,690 A | 5/1996 | Errico et al. |
| 5,569,247 A | 10/1996 | Morrison |
| 5,591,167 A | 1/1997 | Laurain et al. |
| 5,601,553 A | 2/1997 | Trebing et al. |
| 5,601,554 A | 2/1997 | Howland et al. |
| 5,607,427 A | 3/1997 | Tschakaloff |
| 5,607,428 A | 3/1997 | Lin |
| 5,653,710 A | 8/1997 | Harle |
| 5,676,667 A | 10/1997 | Hausman |
| 5,709,686 A | 1/1998 | Talos et al. |
| 5,722,976 A | 3/1998 | Brown |
| 5,752,958 A | 5/1998 | Wellisz |
| 5,822,865 A | 10/1998 | Bosch et al. |
| 6,007,538 A | 12/1999 | Levin |
| 6,129,728 A | 10/2000 | Schumacher et al. |
| 6,315,852 B1 | 11/2001 | Magrini et al. |
| 6,325,803 B1 | 12/2001 | Schumacher et al. |
| 6,488,685 B1 | 12/2002 | Manderson |
| 6,565,570 B2 | 5/2003 | Sterett et al. |
| 6,960,211 B1 | 11/2005 | Pfefferle et al. |
| 7,052,499 B2 | 5/2006 | Steger et al. |
| 2005/0065521 A1 | 3/2005 | Steger et al. |

OTHER PUBLICATIONS

Cheng, Wen et al., Biomechanical Study of Sternal Closure Techniques, Ann Thorac Surg 55:737-740, 1993, The Johns Hopkins Medical Institutions, Baltimore, MD.

Ozaki, Wayne et al., Biomechanical Study of Sternal Closure Using Rigid Fixation Techniques in Human Cadavers, Ann Thorac Surg 65:1660-1665, 1998, University of Michigan Medical Center, Ann Arbor, MI.

Ellis, Edward III et al., Bite Forces Before and After Surgical Correction of Mandibular Prognathism, J Oral Maxillofac Surg 54:176-181, 1996, American Assoc. of Oral and Maxillofacial Surgeons.

Follis, Fabrizio M. et al., Catastrophic Hemorrhage on Sternal Reentry: Still a Dreaded Complication?, Ann Thorac Surg 68:2215-2219, 1999, The Society of Thoracic Surgeons (reprint).

Sherman, John E. et al., Chest Wall Stabilization Using Plate Fixation, Ann Thorac Surg 46:467-469, Oct. 1988, The Society of Thoracic Surgeons.

Youssef, Riad E et al., Comparison of Habitual Masticatory Cycles and Muscle Activity Before and After Orthognathic Surgery, J Oral Maxillofac Surg 55:699-707, 1997, American Assoc. of Oral and Maxillofacial Surgeons.

Sargent, Larry A. et al., The Healing Sternum: A Comparison of Osseous Healing With Wire Versus Rigid Fixation, Ann Thorac Surg 52:490-494, 1991, Plastic Surgery Service, Walter Reed Army Medical Center and Institute of Research, and US Army Institute of Dental Research, Washington, D.C.

Bentz, Michael L. et al., Improved Sternal Fixation in the Correction of Pediatric Pectus Excavatum, Ann Plast Surg 32(6):638-641, Jun. 1994.

Throckmorton, Gaylord S. et al., Improvement of Maximum Occlusal Forces After Orthognathic Surgery, J Oral Maxillofac Surg 54:1080-1086, 1996, American Assoc. of Oral and Maxillofacial Surgeons.

Chase, Christopher W. et al., Internal Fixation of the Sternum in Median Sternotomy Dehiscence, Plast Reconstr Surg. 103(6):1667-1673, May 1999.

McGregor, Walter E. et al., Mechanical analysis of Midline Sternotomy Wound Closure, The Journal of Thoracic and Cardiovascular Surgery, 117(6): 1144-1150, Jun. 1999.

Stoney, William S. et al., Median Sternotomy Dehiscence, The Annals of Thoracic Surgery, 26(5): 421-426, Nov. 1978.

Bryan, A.J. et al., Median Sternotomy Wound Dehiscence: A Retrospective Case Control Study of Risk Factors and Outcome, J.R. Coll Surg Edinb 37(5):305-308, Oct. 1992.

Mayba, I.I., Non-Union of Fractures of the Sternum, The Journal of Bone and Joint Surgery, 67(7):1091-1093, Sep. 1985.

Kitchens, Jerry et al., Open Fixation of Sternal Fracture, Surg Gynecol Obstet. 177(4):423-424, Oct. 1993.

Smoot, E. Clyde et al, Paramedian Sternal Bone Plate Reinforcement and Wiring for Difficult Sternotomy Wounds, Ann Plast Surg 41(5):464-467, Nov. 1998.

Hale, Joseph E. et al., A Polyurethane Foam Model for Characterizing Suture Pull-Through Properties in Bone, Presented at the 23rd Annual Meeting of the American Society of Biomechanics, University of Pittsburgh, Oct. 21-23, 1999, www.asb-biomech.org/abstracts99/133, 4 pages, (reprint).

Miller, Mark D. et al., Repair of Sternal Dehiscence Using a Harrington Compression System, Ann Thorac Surg 45:684-685, Jun. 1988.

Gottlieb, Lawrence J. et al., Rigid Internal Fixation of the Sternum in Postoperative Mediastinitis, Arch Surg 129:489-493, May 1994.

Hendrickson, Steven C. et al., Sternal Plating for the Treatment of Sternal Nonunion, Ann Thorac Surg 62:512-518, 1996.

Song, David H. et al., Sternal Salvage With Quantitative Bacteriology and Rigid Plate Fixation in Postoperative Mediastinitis: A 10 Year Experience, American Assoc. of Plastic Surgeons—79th Annual Meeting, Laguna Niguel, CA, May 7-10, 2000, 3 Pages.

Song, David H., Prophylactic Rigid Plate Fixation for High Risk Sternotomies, The Chicago Society of Plastic Surgery, Chicago, IL, Feb. 23, 2001, 16 pages.

Hazari, Anita et al., Superior Sternal Cleft: Construction With a Titanium Plate, Plast Reconstr Surg. 101(1):167-70, Jan. 1998.

Vincent, Josef G., Update on Sternal Osteosynthesis, Ann Thorac Surg 41:216-218, Feb. 1986.

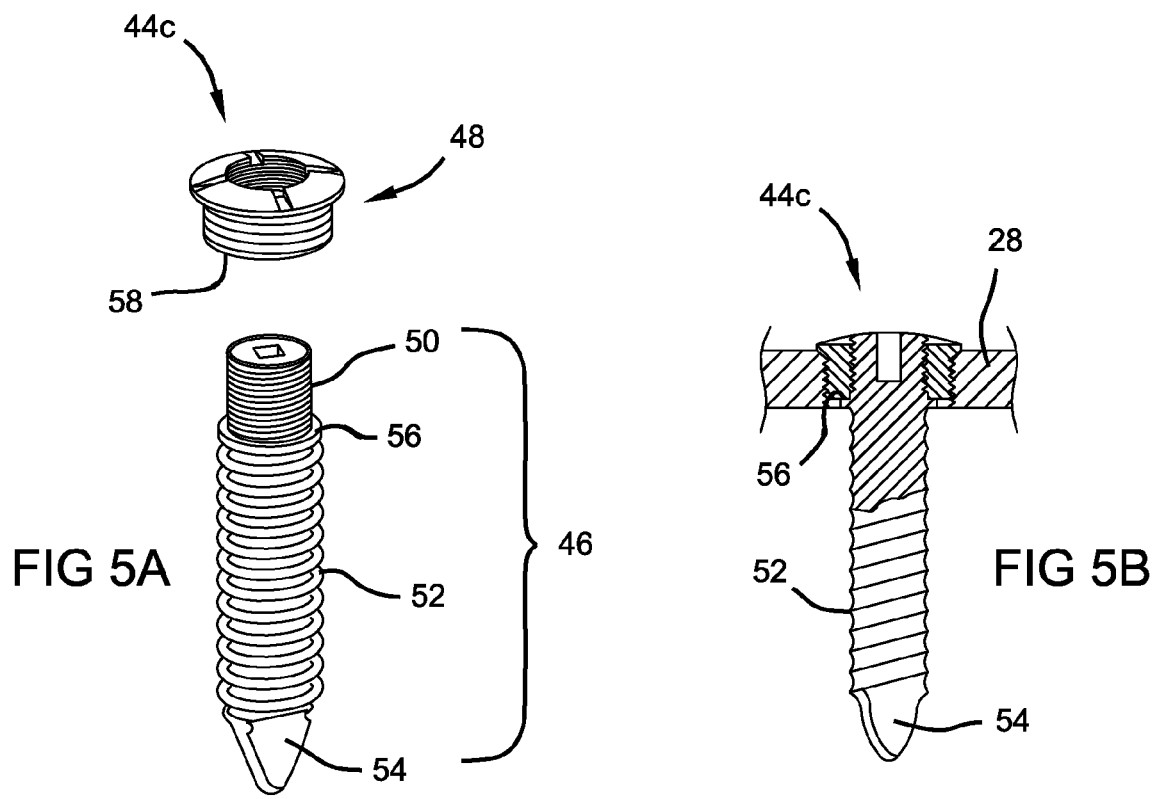
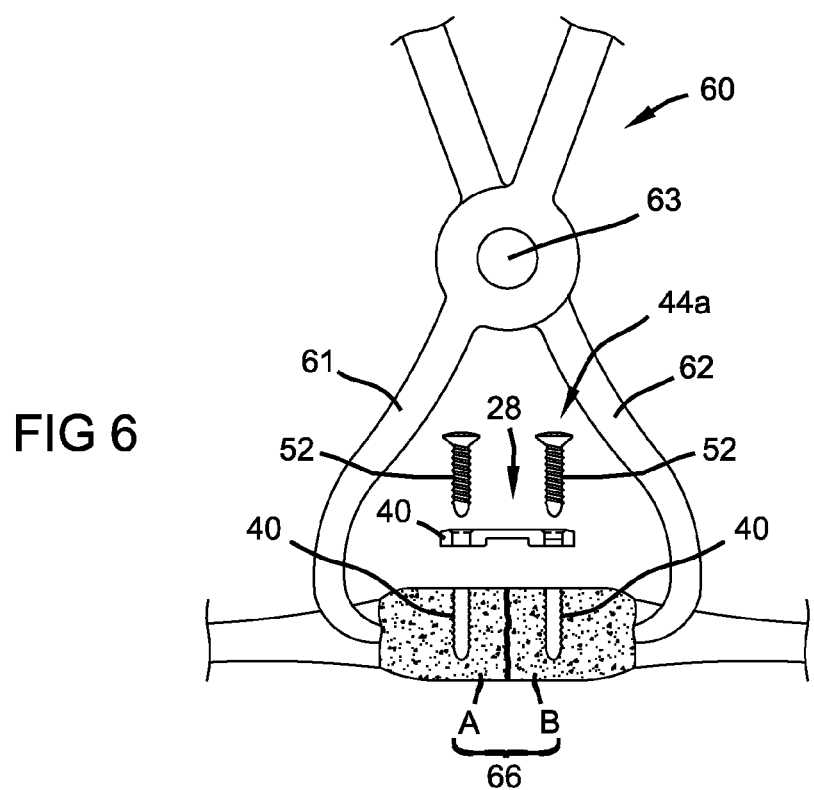

METHOD AND APPARATUS FOR BONE FRACTURE FIXATION

CROSS-REFERENCE TO RELATED APPLICATIONS

This application is a continuation of U.S. patent application Ser. No. 10/980,705, filed on Nov. 3, 2004, which is a continuation-in-part of U.S. patent application Ser. No. 10/081,166, filed on Feb. 22, 2002 (now U.S. Pat. No. 7,052, 499). The disclosure of each of the above applications is incorporated herein by reference.

FIELD

The present teachings relate to surgical applications for the repair of bone fractures and deformities. More particularly, the teachings relate to a method and apparatus for securing two severed bone portions in a relatively fixed relationship to each other.

BACKGROUND

This section provides background information related to the present disclosure which is not necessarily prior art.

In various orthopedic surgical procedures, it is necessary to align and secure two severed bone portions in a relatively fixed relationship to each other. For example, it is often necessary to establish such a secured relationship after a bone has been fractured as a result of either natural causes or physician intervention. To ensure that the bone can regenerate in the proper orientation and fuse the fracture, it is important that the bone portions be fixed in the desired position during bone regeneration.

SUMMARY

A method according to the present disclosure may include determining a load to be supported across separated bone regions by a bridge region of a bone plate. The method may further include determining an acceptable cut force (CF) for the bridge region, determining a cross-sectional area (a) of the bridge region based on the determined load, and determining a height (h) and a width (w) of the bridge region. The height and width may be determined by the following equation:

$$CF = ((S1)(a) + C1)\left(\frac{w}{h_{max}}\right)^{S2}$$

wherein S1, C1, and S2 are constants for a given bridge material. Constant S1 is a slope of a curve defined by a range of cut force versus cross-sectional area. Constant C1 is a Y-intercept of the curve, and constant S2 is a slope of Ln (ARF) versus Ln (aspect ratio). ARF is an aspect ratio factor defined by:

$$ARF = \frac{CF1}{(CF1 + CF2)/2}$$

wherein ($h_{max}$) is a maximum height of the bridge region. CF1 is a first cut force associated with one of the width (w) and the maximum height ($h_{max}$) of the bridge region. CF2 is a second cut force associated with the other of the width (w) and the maximum height ($h_{max}$). The aspect ratio is a ratio between the maximum height ($h_{max}$) and the width (w). The method may further include providing a bone plate including a bridge region having the height (h) and width (w) for securing the separated bone regions.

The determined acceptable cut force (CF) may be a maximum allowable cut force for the bridge region.

The method may further include removing the bone plate from a sternum by severing the bridge region with a cutting tool. The severing may include cutting along the width (w). The method may further include securing the plate to the separated bone region. The plate may include a first fixation region on a first end of the bridge region and a second fixation region on a second end of the bridge region. The securing may include fixing the first fixation region to a first side of the separated bone region and fixing the second fixation region to a second side of the separated bone region. The first fixation region may include a hook and the securing may include locating the hook around the first side of the separated bone region.

The method may further include securing the plate to a separated sternum. The plate may include a first fixation region on a first end of the bridge region and a second fixation region on a second end of the bridge region. The securing may include coupling the first fixation region to a first side of the separated sternum and coupling the second fixation region to a second side of the separated sternum. The first fixation region may include a hook and the securing may include locating the hook around the first side of the separated sternum.

The cross-sectional area (a) may be defined by the product of the maximum height ($h_{max}$) and the width (w). The determined height (h) may be less than or equal to the maximum height ($h_{max}$). The first cut force (CF1) may be defined along the width (w). Alternatively, the first cut force (CF1) may be defined along the height (h).

According to the present disclosure, a bone plate may include a first fixation region adapted to secure the bone plate to a first side of a separated bone region, a second fixation region adapted to secure the bone plate to a second side of the separated bone region, and a bridge region extending between and coupling the first and second fixation regions to one another. The bridge region may define a cross-sectional area (a) separable by a predetermined maximum allowable cut force (CF). The bridge region may support a predetermined load across the separated bone region and may be defined by:

$$CF = ((S1)(a) + C1)\left(\frac{w}{h_{max}}\right)^{S2}$$

and may have a width (w) and a height (h) that is less than or equal to a maximum height ($h_{max}$). S1, C1, and S2 are constants for a given bridge material. Constant S1 is a slope of a curve defined by a range of cut force versus cross-sectional area. Constant C1 is a Y-intercept of the curve. Constant S2 is a slope of Ln (ARF) versus Ln (aspect ratio). ARF is an aspect ratio factor that is defined by:

$$ARF = \frac{CF1}{(CF1 + CF2)/2}$$

where CF1 is a first cut force associated with one of the width (w) and the maximum height ($h_{max}$) of the bridge region. CF2 is a second cut force associated with the other of the width (w)

and the maximum height ($h_{max}$). The aspect ratio is the ratio between the maximum height ($h_{max}$) and the width (w).

The first fixation region may include a hook adapted to extend around the first side of a separated bone region. The second fixation region may include a first aperture adapted to receive a first fastener to couple the bone plate to the second side of the separated bone region. The first fixation region may include a second aperture located between the bridge region and the hook and adapted to receive a second fastener to couple the bone plate to the second side of the separated bone region. The hook may be adapted to extend around a first side of a separated sternum.

The cross-sectional area (a) may be defined by the product of the maximum height ($h_{max}$) and the width (w). The first cut force (CF1) may be defined along the width (w). Alternatively, the first cut force (CF1) may be defined along the height (h).

Further areas of applicability of the present teachings will become apparent from the detailed description provided hereinafter. It should be understood that the detailed description and specific examples, while indicating the preferred embodiments of the teachings, are intended for purposes of illustration only and are not intended to limit the scope of the teachings.

BRIEF DESCRIPTION OF THE DRAWINGS

FIG. 1 illustrates a previously severed sternum coupled by a plate in one possible placement scheme according to the teachings;

FIG. 5A is an exploded perspective view of a two-piece fastener used to secure the plate of FIG. 1 to a severed bone portion;

FIG. 5B is a side view of the fastener of FIG. 5A, the fastener seated within an aperture of the plate of FIG. 1;

FIG. 6 is a partially sectioned side view of the plate of FIG. 1 illustrating the cooperation of the plate with the fasteners of FIG. 4 for securing the plate to the previously severed sternum halves, wherein the previously severed sternum halves have been reapproximated using the illustrated surgical forceps;

DETAILED DESCRIPTION

The following description is merely exemplary in nature and is in no way intended to limit the teachings, its application, or uses.

Figure 1:
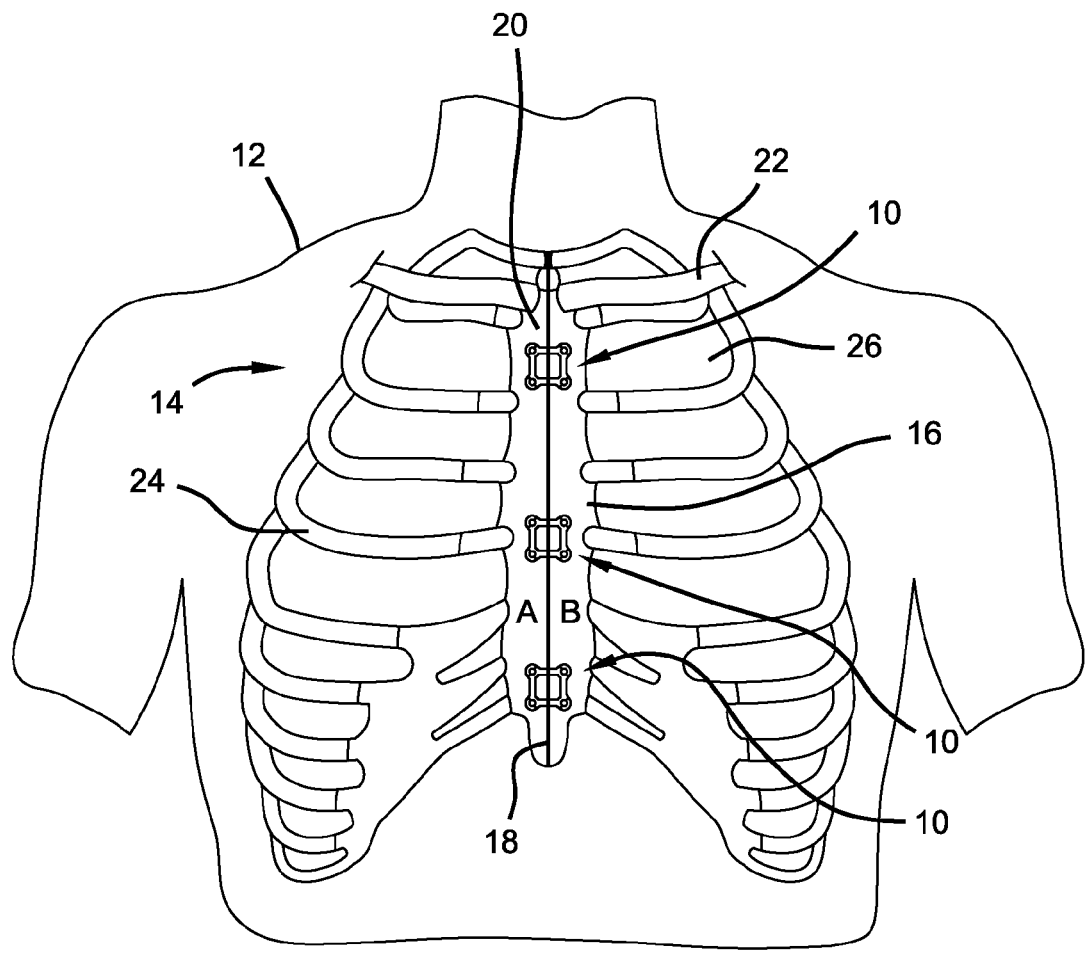
FIG. 1 is a perspective post-operative anterior illustration of a human thorax. Specifically.

Referring to FIG. 1, a system constructed in accordance with the present teachings is generally identified with reference numeral 10. The system 10 is shown operatively associated within a human body 12 and specifically a human thorax 14. However, it will become apparent to those skilled in the art that certain aspects of the present teachings have applicability to other surgical applications.

The anterior of the thorax 14 is formed by a sternum 16, xyphoid 18, manubrium 20, costal cartilage, and ribs 24. In addition, the clavicle 22 is shown connecting the sternum 16 to the scapula and humerus (neither shown). The sternum 16, as shown, has previously undergone a medical procedure known as a median sternotomy. As a result of this procedure, the sternum 16 has been severed, thus permitting physician access to the tissues or organs located in thoracic cavity 26. However, the sternum 16 has since been reapproximated with previously severed portions A and B now bound together by the system 10 of the present teachings.

Figure 2:
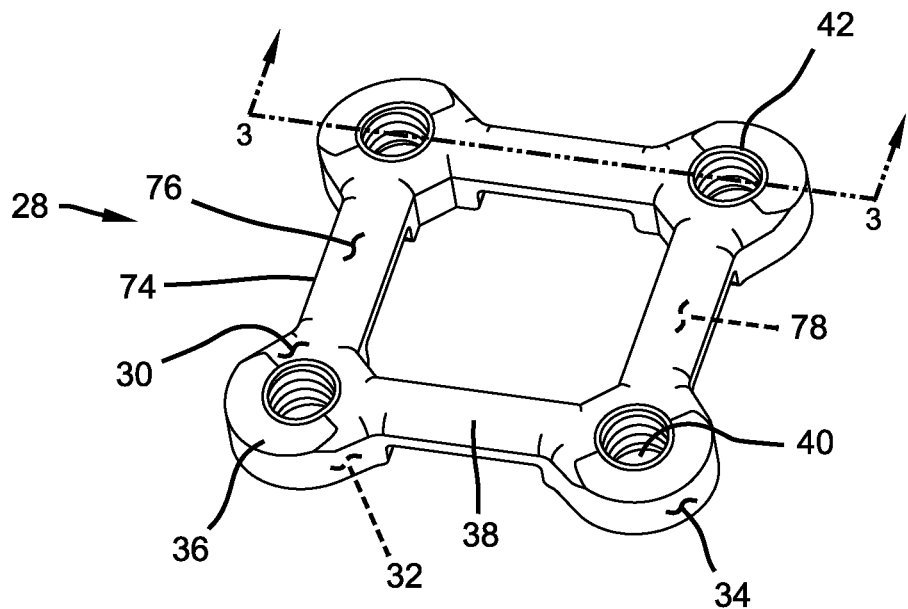
FIG. 2 is a perspective view of the plate of FIG. 1.

With continued reference to FIG. 1 and additional reference to FIGS. 2 through 19, the system 10 of the present teachings is shown to include a plate 28. The plate 28 is shown to include an upper surface 30, a lower surface 32, and a perimeter surface 34. The perimeter surface 34 may be specifically defined, as seen in FIG. 2, or may simply be the point at which the upper surface 30 and the lower surface 32 meet. The plate 28 is divided into varying regions such as at least two bone fixation regions 36 and at least one bridge region 38.

Figure 3:
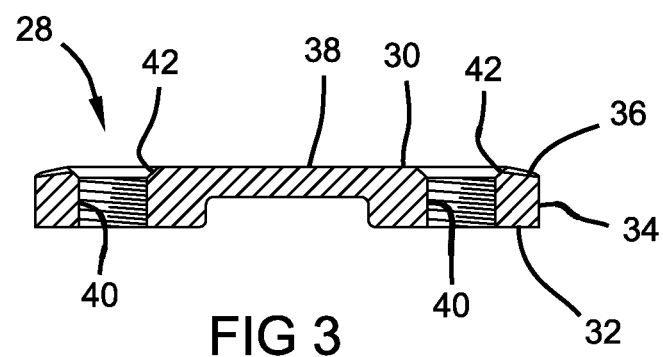
FIG. 3 is a cross-sectional view taken along line 3-3 of FIG. 2.

The bridge region 38 joins the bone fixation regions 36 and may be disposed generally flush with either, or both, of the upper or lower surfaces 30, 32 or may be offset from both of the upper and lower surfaces 30, 32, as will be discussed further below. Each bone fixation region 36 defines at least one aperture 40. The apertures 40 may be threaded or simply formed as non-threaded through holes. The apertures 40 may extend symmetrically from the bridge region 38 or may be arranged asymmetrically. Further, the apertures 40 may optionally include a circular or an oval countersink 42 and may be internally threaded, as best shown in FIGS. 2 and 3. The apertures 40 are adapted to receive a fastener 44a-c for interconnecting the plate 28 with a severed bone region, such as severed halves A and B of the sternum 16. More specifically, the bridge region 38 spans the fracture while bone fixation regions 36 are fastened to the bone regions on either side of the fracture once the severed halves A and B have been reapproximated.

The plate 28 described in any of the embodiments of the present teachings may be made of a variety of bio-resorbable materials. One resorbable material of particular interest is marketed by Biomet, Inc. (Warsaw, Indiana) under the tradename LACTOSORB®. LACTOSORB® is an absorbable copolymer synthesized from all-natural ingredients: 82% L-lactic acid and 18% glycolic acid, and is substantially amorphous (i.e., without crystallinity), meaning that its degradation is uniform, precluding the crystalline release associated with degrading copolymers that have been associated with late inflammatory reactions. Furthermore, the LACTOSORB® copolymer ratio permits the polymer to retain most of its strength for six to eight weeks. Such a time period is appropriate for healing, but not so long as to raise concerns about long-term stress shielding of bone. In addition to LACTOSORB®, other resorbable materials may be used such as PLA, PGA, and others including various polymers, ceramics, etc.

The plate 28 may also be made from a variety of bio-compatible materials. Examples of bio-compatible materials that may be used are the implantable plastics PEEK or PET. In addition to PEEK or PET, implantable surgical metals may also be used. Alloys that may be implanted are, but not limited to, stainless steel, titanium, or cobalt chrome molybdenum. Specifically, commercially pure titanium, listed as grade 1, 2, 3, or 4 or titanium alloy such as titanium 6-aluminum/4-vanadium may be used. The plate 28 may be inelastically deformable so as to retain its shape once contoured to cooperate with the shape of the bone regions to be secured.

With particular reference to FIGS. 4A-4D, a fastener 44a is provided for use with the plate 28. The fastener 44a is a one-piece, locking fastener and is designed so as to matingly engage the threaded apertures 40 of bone fixation regions 36. The fastener 44a is considered a locking fastener as the engagement between threads 52 on the fastener 44a and the threaded aperture 40 prevents relative movement therebetween. As can be appreciated, preventing relative movement between the plate 28 and the fastener 44a helps ensure that the plate 28 remains in a desired position relative to the bone halves A, B.

With particular reference to FIGS. 4A-4D, a second fastener 44b is provided for use with the plate 28. The fastener 44b is a one-piece, non-locking fastener and is received by apertures 40b formed through the respective bone fixation regions 36 of the plate 28. The fastener 44b is substantially identical to fastener 44a, but is considered a non-locking fastener due to the relationship between the plate 28 and the fastener 44b. Specifically, because apertures 40b are simply bores formed through the respective bone fixation regions 36 of the plate 28, and as such, do not include threads, the relationship between the fasteners 44b and the plate 28 is considered "non-locking." As can be appreciated, such a relationship may provide a cost advantage to the plate 28 as the additional cost associated with forming threads in the apertures 40b is obviated.

With reference to FIGS. 5A-5B, a third fastener 44c of the present teachings is shown to generally include a main body 46 and a head member 48. The main body 46 includes an upper shaft portion 50 and a lower shaft portion 52. The lower shaft portion 52 is externally threaded, fluted, and preferably fitted with a pointed end portion 54 so as to permit self-drilling of the sternum 16 by fastener 44. Insertion of the lower shaft portion 52 into sternum 16 is limited by a flange 56 interdisposed between the upper and lower shaft portions 50 and 52. The upper shaft portion 50 is also externally threaded and adapted to engage an internally threaded aperture 58 of the head member 48. The head member 48 is externally threaded for engaging one of the plurality of internally threaded apertures 40 of the plate 28.

In one application, the thread pitches of the upper shaft portion 50, lower shaft portion 52, and the thread pitch of the external threads of the head member 48 are common. The external threads of the head member 48 and the externally threaded lower shaft portion 52 have a common thread lead. In the exemplary embodiment illustrated, the externally threaded lower shaft portion 52 has a single lead configuration while the external threads of the upper shaft portion 50 and head member 48 have a double lead configuration. The use of faster 44c is advantageous because it allows the plate 28 to be removed while the lower portion 52 remains in place in the event that the plate 28 must be removed. This retains the integrity of each hole formed in the bone and eliminates the need to remove and re-insert different fastening devices into the bone each time the plate 28 is removed and re-seated.

Fasteners 44a-c may be formed of a suitably rigid biocompatible material. However, if the intent is to insert fasteners 44a-c into the bone for a temporary period of time, it may be formed from a bio-resorbable material. Fasteners 44a-c formed from bio-resorbable materials degrade within the body, thus eliminating the need for subsequent removal of the fasteners 44a-c.

Figure 4A:
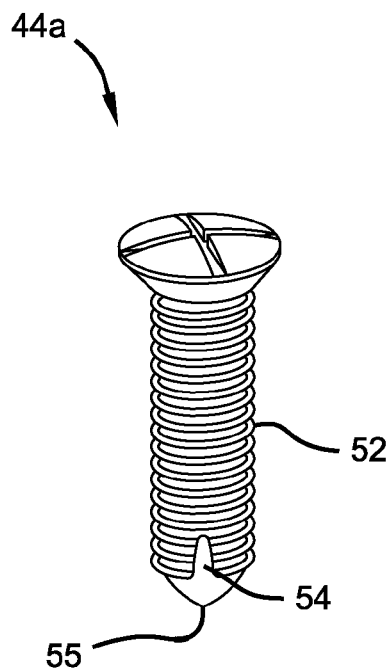
FIG. 4A is a perspective view of a one-piece, self-tapping fastener used to secure the plate of FIG. 1 to a severed bone portion.
Figure 4B:
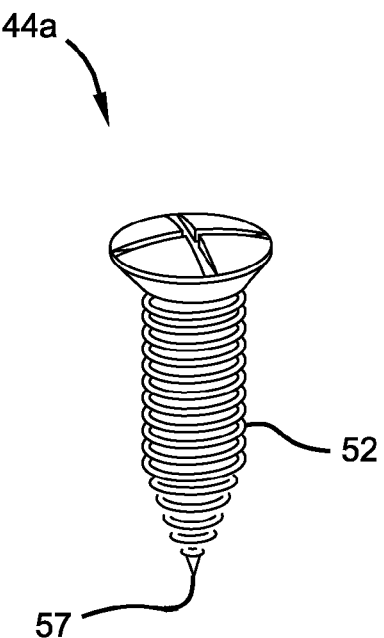
FIG. 4B is a perspective view of the fastener of FIG. 4A incorporating a self-drilling tip.
Figure 4C:
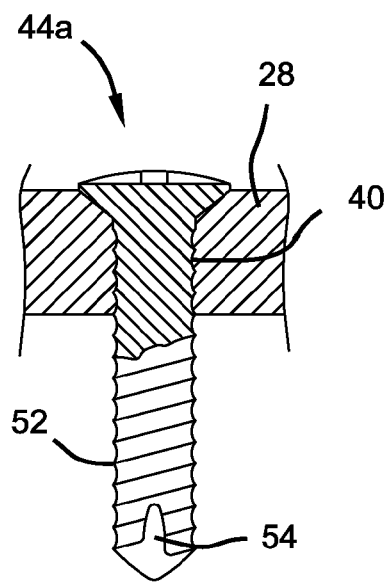
FIG. 4C is a cross-sectional view of the fastener of FIG. 4A, the fastener seated within a threaded aperture of the plate of FIG. 1.
Figure 4D:
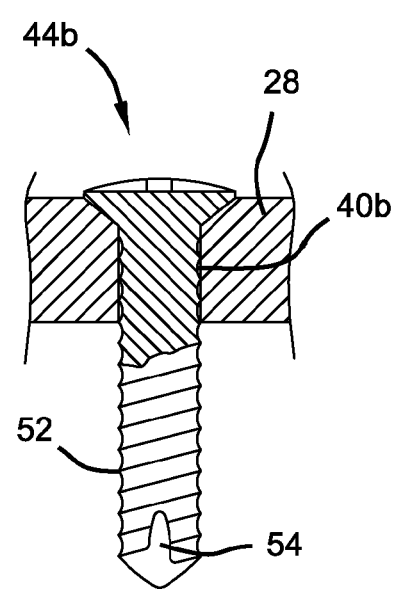
FIG. 4D is a cross-sectional view of the fastener of FIG. 4A, the fastener seated within an aperture of the plate of FIG. 1.
Figure 7:
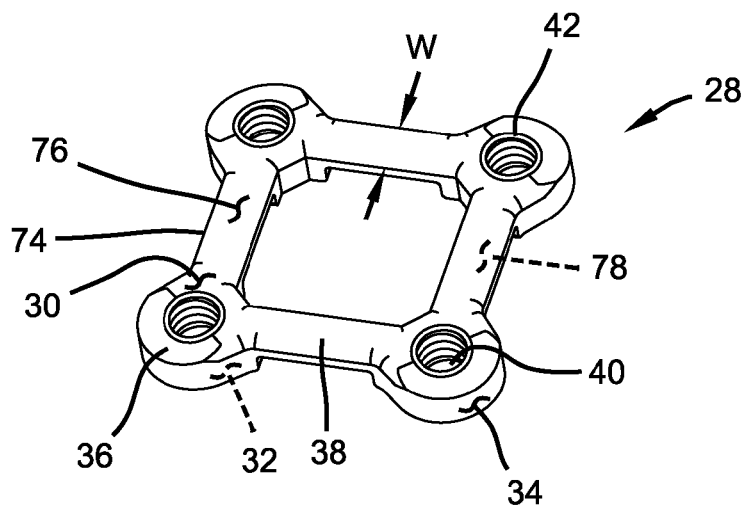
FIG. 7 is a perspective view of a plate according to the present teachings, the plate having four bone securing regions and a bridge region spanning between each bone securing region.

It should be noted that any of the foregoing fasteners 44a-c may include a self-tapping feature and/or a self-drilling feature. A self-tapping tip 55 is used to create a series of threads in the receiving bone, as best shown in FIG. 4A while a self-drilling tip 57 is used to create a bore in the receiving bone, as best shown in FIG. 4B. It should be understood that while the fasteners 44a, 44b may include either tip 55, 57, that the self-drilling tip 57 may further incorporate a self-tapping feature such that as the generally sharp tip 57 creates a bore in the receiving bone, the tip 57 concurrently cuts a series of threads therein for engagement with the threads 52 of the respective fastener 44a, 44b. Because each fastener 44a-c is inserted through an aperture 40 formed in the bone fixation region 36 of the plate in a similar fashion, fastener 44a will be used herein after when discussing the attachment of the plate 28 to the respective bone halves A, B.

In use, before the plate 28 may be secured to severed halves A and B of sternum 16, the severed halves A and B must be reapproximated. Reapproximation of severed sternum halves A and B may be carried out using, as seen in FIG. 6, a reapproximation device, such as surgical forceps 60. The surgical forceps 60 are comprised of two jaws 61, 62 that are interconnected at actuation point 63. The jaws 61, 62 are able to laterally hook separated bone halves A and B. By pivoting the jaws 61, 62 about actuation point 63, a physician is able to decrease the distance between the jaws 61, 62 and thus, in turn, decrease the distance between the separated bone halves A and B.

Once the separated bone halves A and B have been reapproximated, the plate 28 is positioned on the bone surfaces to be coupled so that certain apertures 40 may be selectively used as a guide for drilling holes (not specifically shown) in the bone surfaces for receiving the fasteners 44a.

A first of the fasteners 44a is passed through a selected one of the apertures 40 and rotated so that the externally threaded lower portion 52 is driven into the hole (not shown) in one of the halves A or B of the sternum 16. For example, as the externally threaded lower portion 52 of the fastener 44a is driven into the sternum 16, the external threads 52 simultaneously engage the internally threaded aperture 40 of the plate 28. In addition, the fastener may also self-drill and/or self-tap the bone half A, B, depending on the particular tip 55, 57 of the fastener 44a, as previously discussed.

Additional fasteners 44a are used to interconnect the plate 28 with the sternum 16 in a substantially identical manner. However, it will become appreciated by those skilled in the art that any number of fasteners 44a may be employed depending on a particular application.

After the plate 28 has been secured into place, it may be necessary to remove the plate 28 so as to allow a physician to re-separate the sternum 16 and gain access to either the sternum 16 or the thoracic cavity 26 to provide treatment (e.g., emergency or planned secondary cardiac surgery). To facilitate removal of the plate 28, the fasteners 44a are unthreaded and removed from the apertures 40 of the respective bone fixation regions 36. When the plate 28 is removed, it retains its shape due to the inelastic deformation.

When the secondary surgical procedure is complete, the separated halves A and B of the sternum 16 are again reapproximated using the surgical forceps 60 in the manner described above. Once the separated halves A and B of sternum 16 are reapproximated to a desired distance, the halves A and B are held into place by replacing plate 28. The plate 28 is replaced by inserting the fasteners 44a through the selective apertures 40 of the bone fixation regions 36 and simultaneously threading the internal threads of the aperture 40 with the external threads 52 of the fastener 44a.

Referring to FIGS. 9 and 10a-10c, a plate 28a according to the present teachings is shown. Plate 28a is generally similar to plate 28 and thus a detailed description of plate 28a is not necessary. However, unlike plate 28, plate 28a contains extended bone fixation regions 36a having a plurality of apertures 40. It should be noted that plate 28a also includes bridge regions 38 that connect the respective bone fixation regions 36a.

Referring to FIGS. 11 and 12a-12c, a plate 28b according to the present teachings is shown. Plate 28b is generally similar to plate 28 and thus a detailed description of plate 28b is not necessary. However, unlike plate 28, plate 28b includes a single bridge region 38 extending between two bone fixation regions 36b. Again, the bridge region 38 extends generally over the bone fracture region while the bone fixation regions 36b are securely attached to respective halves A and B by fasteners 44.

Figure 13:
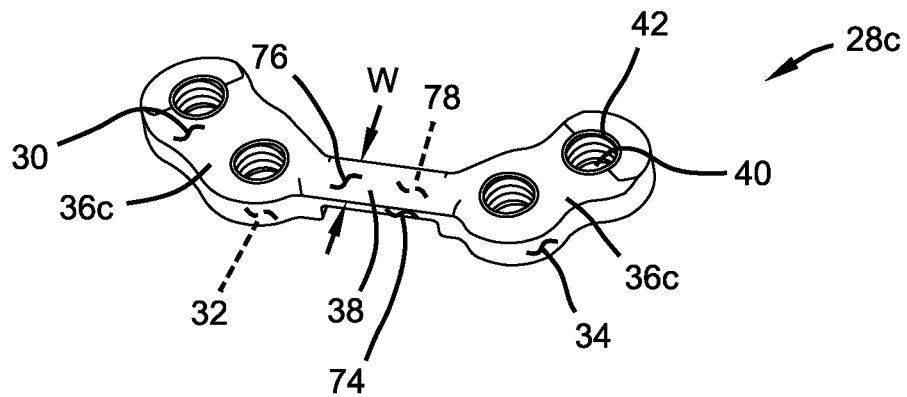
FIG. 13 is a perspective view of a plate according to the present teachings, the plate having two bone securing regions and a bridge region.
Figure 14A:
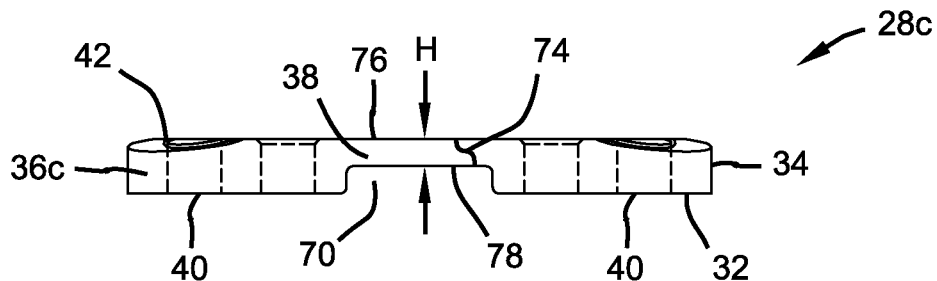
FIG. 14A is a side view of the plate of FIG. 13 showing a bridge design in accordance with the principals of the present teachings.
Figure 14B:
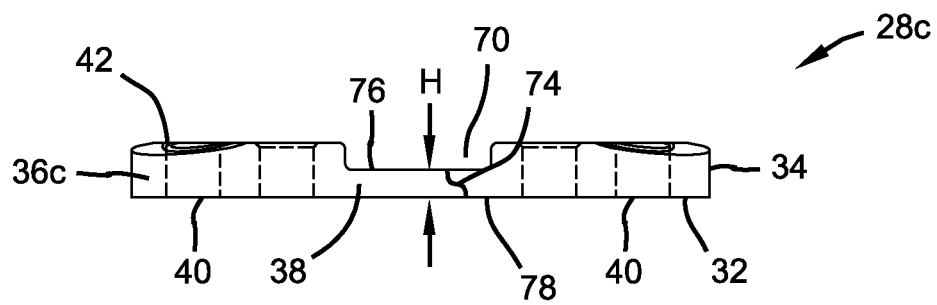
FIG. 14B is a side view of the plate of FIG. 13 showing a bridge design in accordance with the principals of the present teachings.
Figure 14C:
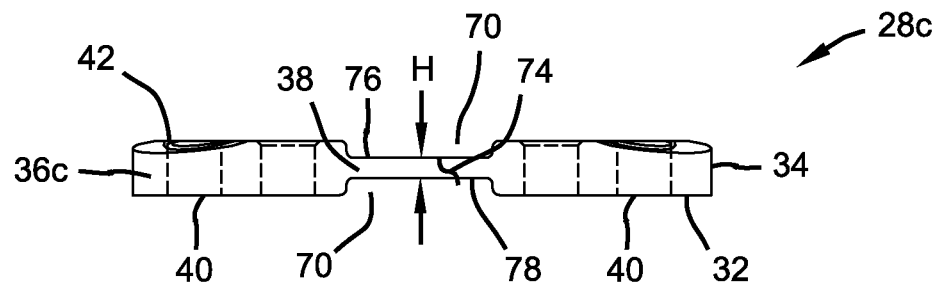
FIG. 14C is a side view of the plate of FIG. 13 showing a bridge design in accordance with the principals of the present teachings.

Referring to FIGS. 13 and 14a-14c, a plate 28c according to the present teachings is shown. Plate 28c is generally similar to plate 28 and thus a detailed description of plate 28c is not necessary. However, unlike plate 28, plate 28c includes a single bridge region 38 extending between two bone fixation regions 36c. The bone fixation regions 36c are formed at an angle relative to the bridge region 38, as best shown in FIG. 13. The bone fixation regions 36c are formed at an angle relative to the bridge region 38 to better fit onto the sternum 16 and to allow for the fixation of transverse fractures. It should be noted that any of the other embodiments of the present teachings may have an orientation between the bone fixation regions 36c and bridge region 38 similar to that of plate 28c.

Figure 15:
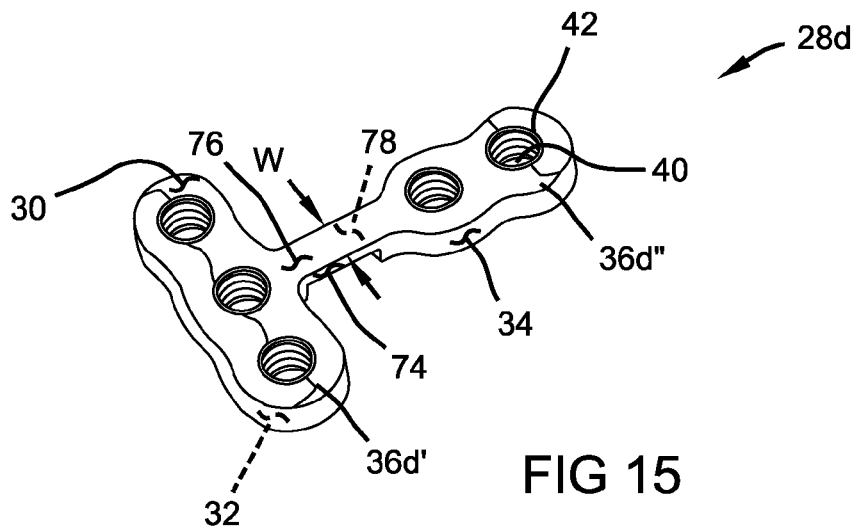
FIG. 15 is a perspective view of a plate according to the present teachings, the plate having two bone securing regions and a bridge region.
Figure 16A:
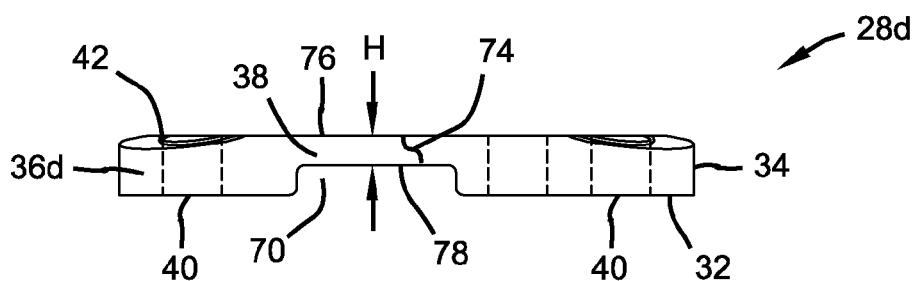
FIG. 16A is a side view of the plate of FIG. 15 showing a bridge design in accordance with the principals of the present teachings.
Figure 16B:
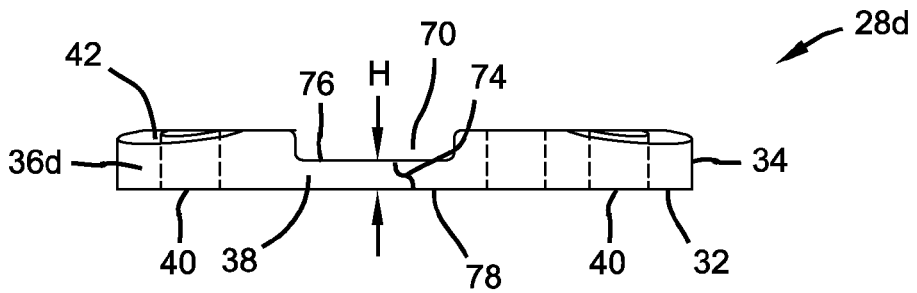
FIG. 16B is a side view of the plate of FIG. 15 showing a bridge design in accordance with the principals of the present teachings.
Figure 16C:
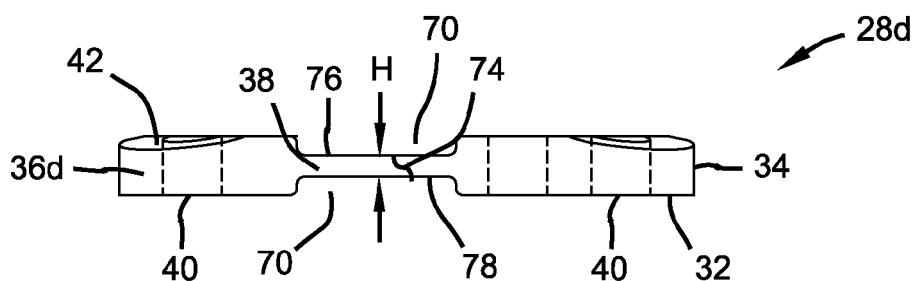
FIG. 16C is a side view of the plate of FIG. 15 showing a bridge design in accordance with the principals of the present teachings.

Plate 28d is illustrated in FIGS. 15 and 16a-16c and is in accordance with the present teachings. Plate 28d is generally similar to plate 28 and thus a detailed description of plate 28d is not necessary. Plate 28d is different from plate 28 in that plate 28d includes a single bridge region 38 extending generally between two bone fixation regions 36d. The bone fixation regions 36d are substantially similar to those of plate 28, except that the bone fixation regions of plate 28d are disposed in an opposite relationship relative to one another. Specifically, a first bone fixation region 36d' runs generally perpendicular to the bridge region 38 while a second bone fixation region 36d" runs generally parallel with the bridge region 38, as best shown in FIG. 15.

Bone fixation region 36d" includes a total of three apertures 40 while bone fixation region 36d' includes two apertures 40 for use in attachment to respective bone halves A, B. The extra aperture 40 provided on fixation region 36d" allows for an extra fastener to securely fix the fixation region 36d" to a respective bone halve A, B. Therefore, the extra aperture 40 and corresponding fastener 44a serves to restrict fastener pull-through and helps to ensure that the plate 28 remains fixed to the bone halves A, B.

In each of the foregoing plates 28, 28a, 28b, 28c, and 28d, the bridge region 38 may be offset from the bone fixation regions so as to form a recess 70 either between the upper surface 30 and the bridge region 38, between the lower surface 32 and the bridge region 38, or between both surfaces 30, 32 and the bridge region 38, as best shown in FIGS. 8a-c, 10a-c, 12a-c, 14a-c, and 16a-c. However, it should be noted that the bridge region 38 could include upper and lower surfaces 76, 78 that are generally planar with the upper and lower surfaces 30, 32 of the bone fixation regions 36, whereby the width W is small enough so as to allow the bridge region 38 to be severed in an emergency, as will be discussed further below. The bridge region 38 provides each plate 28, 28a, 28b, 28c, and 28d with the requisite strength between the bone halves A, B while the recess 70, or with W of the bridge region 38, concurrently provides a physician or surgeon with the ability to quickly cut the bridge region 38 to quickly remove the plate 28, 28a, 28b, 28c, and 28d. Because each plate 28, 28a, 28b, 28c, and 28d includes a substantially identical bridge region 38, reference will be made to plate 28 when describing the bridge region 38 hereinafter.

Figure 17:
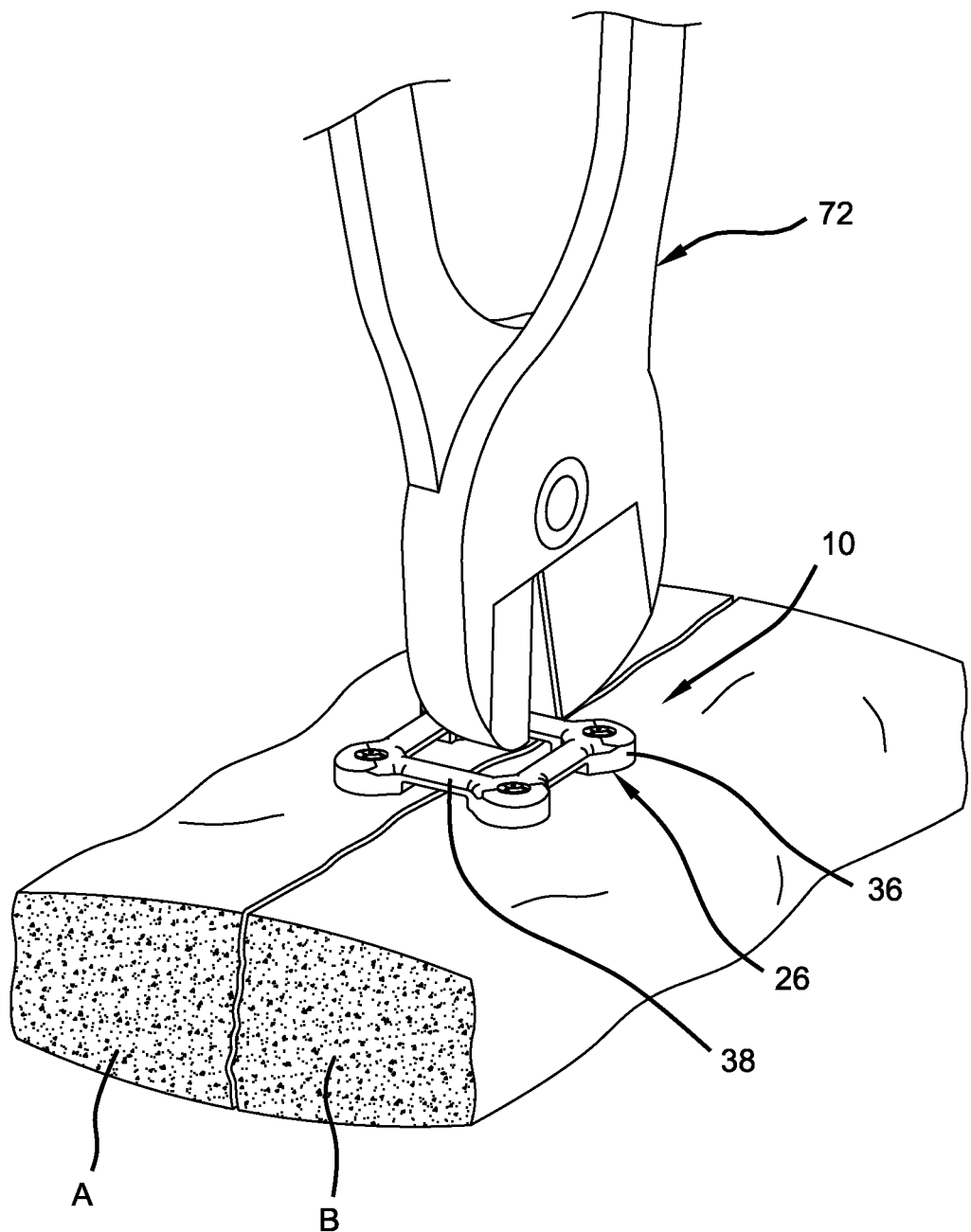
FIG. 17 is a perspective view of the plate of FIG. 7 with a bridge region of the plate engaged by plate cutter, wire cutter, or surgical scissors.

The recess 70 may be easily engaged by a cutting device such as surgical scissors 72, wire cutters, plate cutters, or a cautery (only applicable for non-metal fixation) so as to permit the scissors 72, wire cutters, plate cutters, or cautery to sever the bridge region 38, as best shown in FIG. 17. Consequently, the plate 28 permits a physician or surgeon access to the thoracic cavity 26 by removing the fasteners 44a or by severing the bridge region 38.

Figure 8A:
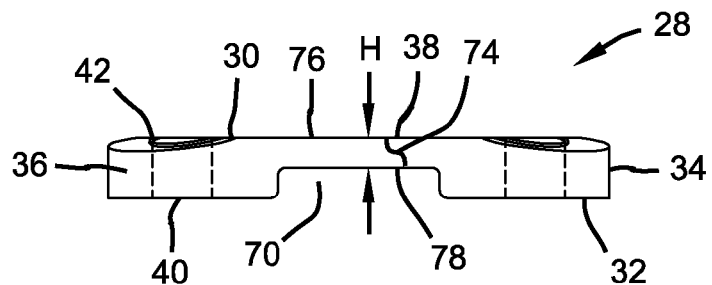
FIG. 8A is a side view of the plate of FIG. 7 showing a bridge design in accordance with the principals of the present teachings.
Figure 8B:
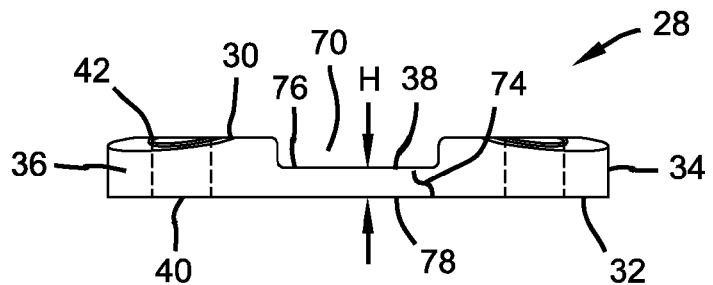
FIG. 8B is a side view of the plate of FIG. 7 showing a bridge design in accordance with the principals of the present teachings.
Figure 8C:
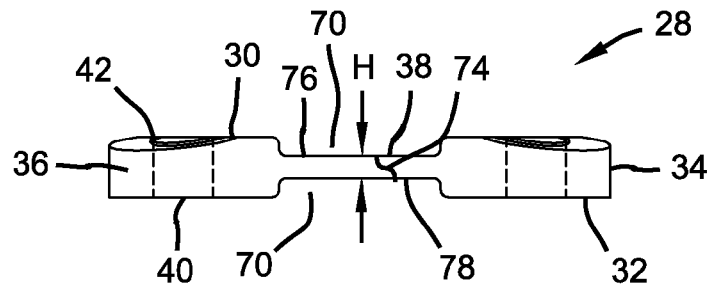
FIG. 8C is a side view of the plate of FIG. 7 showing a bridge design in accordance with the principals of the present teachings.
Figure 9:
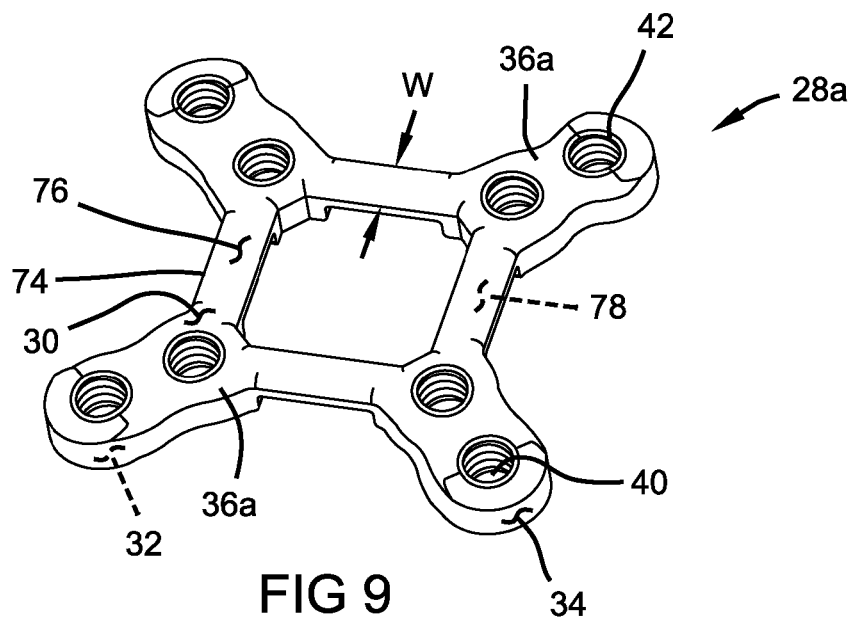
FIG. 9 is a perspective view of a plate according to the present teachings, the plate having four bone securing regions and a bridge region spanning between each bone securing region.
Figure 10A:
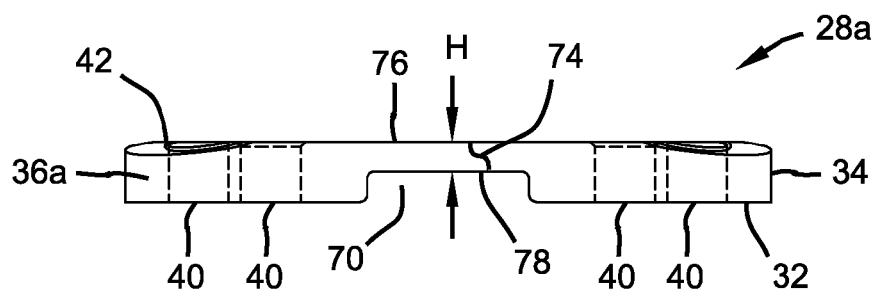
FIG. 10A is a side view of the plate of FIG. 9 showing a bridge design in accordance with the principals of the present teachings.
Figure 10B:
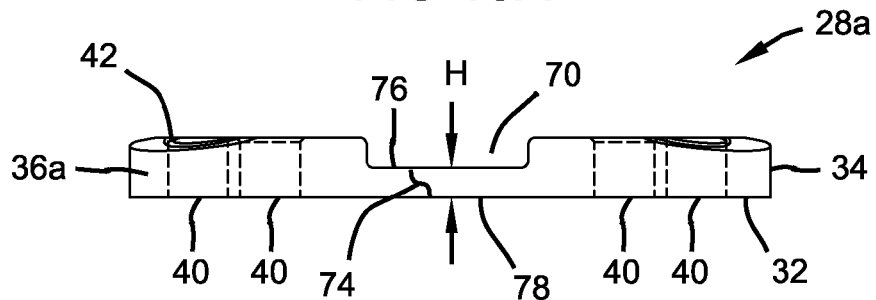
FIG. 10B is a side view of the plate of FIG. 9 showing a bridge design in accordance with the principals of the present teachings.
Figure 10C:
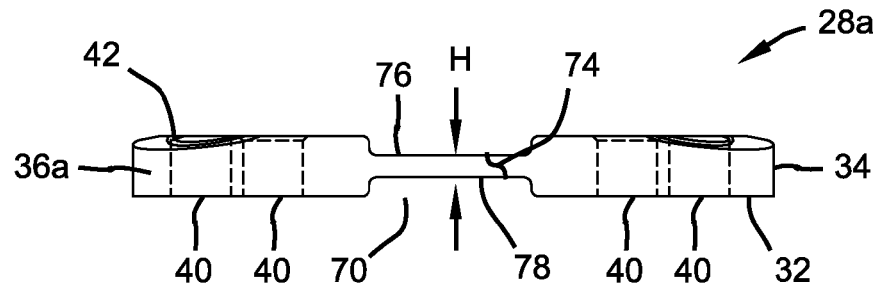
FIG. 10C is a side view of the plate of FIG. 9 showing a bridge design in accordance with the principals of the present teachings.
Figure 11:
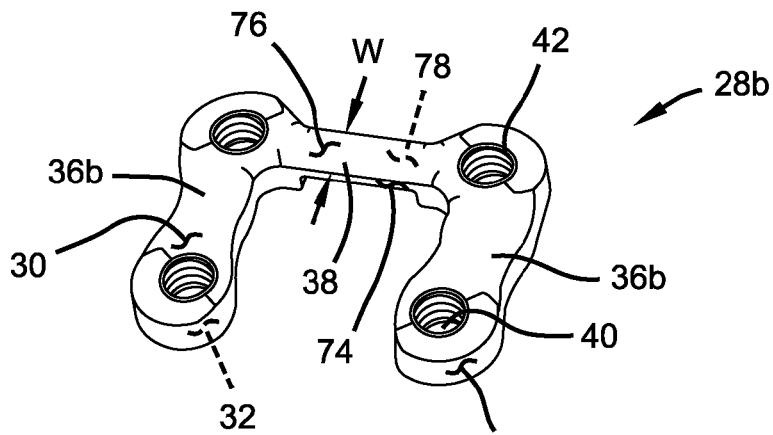
FIG. 11 is a perspective view of a plate according to the present teachings, the plate having two bone securing regions and a bridge region.
Figure 12A:
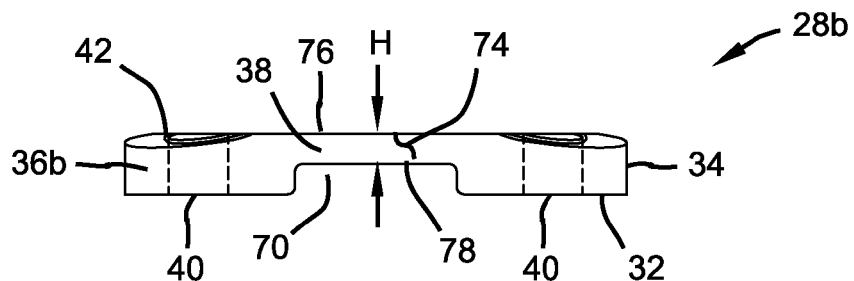
FIG. 12A is a side view of the plate of FIG. 11 showing a bridge design in accordance with the principals of the present teachings.
Figure 12B:
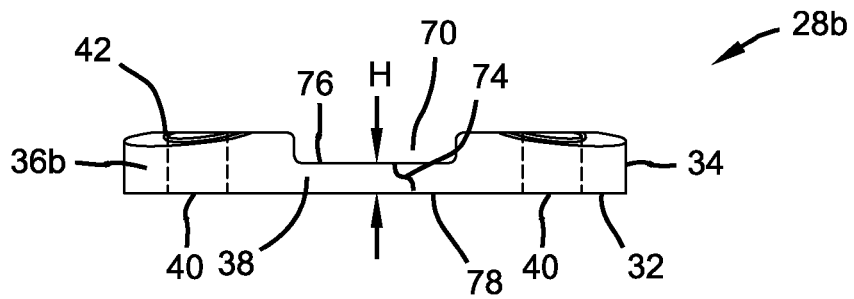
FIG. 12B is a side view of the plate of FIG. 11 showing a bridge design in accordance with the principals of the present teachings.
Figure 12C:
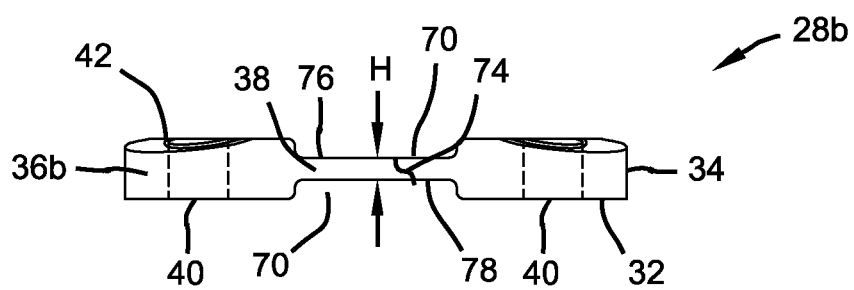
FIG. 12C is a side view of the plate of FIG. 11 showing a bridge design in accordance with the principals of the present teachings.

The bridge region 38 may be tapered at its perimeter surface 74, its upper surface 76, or its lower surface 78 to allow the bridge region 38 to be severed more easily and to provide a smooth surface for added patient comfort. Tapering of the upper surface 76 and the perimeter surface 74 relatively weakens the bridge region 38 and forms the recess 70 generally between upper surface 30 of the bone fixation regions 36 and the upper surface 76 of the bridge region 38, as best shown in FIG. 8a. Tapering of the lower surface 78 results in the formation of the recess 70 generally between the lower surface 32 of the bone fixation regions 36 and the lower surface 78 of the bridge region 38, as best shown in FIG. 8b. In addition, the recess 70 may be formed proximate to both the upper and lower surfaces 76, 78 of the bridge region 38, as best shown in FIG. 8c. It should be noted that while FIG. 17 illustrates plate 28 as having a generally rectangular bridge region 38, alternate embodiments may contain a bridge that is elliptical, oval, or of another cross-section shape that will facilitate engagement of the bridge by a suitable cutting device such as surgical scissors 72 or wire cutters. Further, it is envisioned that any of the other embodiments of the present teachings may include a bridge region 38 that is cylindrical, elliptical, oval, square, or of another cross-section shape so as to facilitate engagement of the bridge by a suitable cutting device.

While the bridge region 38 may include a plurality of varying cross-sectional shapes such as elliptical, oval, or rectangular, the bridge region 38 must be designed so as to accommodate the force requirements with respect to holding the bone halves A, B together while concurrently allowing a physician or surgeon to easily and quickly remove the plate 28 under exigent circumstances. The bridge region 38 is designed to accommodate both requirements (i.e., strength and severability), by balancing strength requirements with cutability requirements in designing the cross-sectional shape. The latter design feature maintains requisite strength properties while providing for quick and easy removal.

The relationship between the requisite force required to sever the bridge region 38 and the cross-sectional area of the bridge region 38 is substantially linear. Therefore, the larger the cross-sectional area of the bridge region 38, the greater the force required to sever the bridge region 38. The cross-sectional area of the bridge region 38 is deigned to both accommodate the strength requirements of the system 10 and to optimize the severability of the bridge region 38.

Optimum bridge severability can be substantially manipulated for a given cross-sectional area, accomplished mainly through manipulation of the aspect ratio of the cross-section of the bridge region 38. The aspect ratio is generally defined as the height H of the plate 28 in the cutter 72 divided by the width W of the plate 28 in the cutter 72. The height of the bridge region 38 is generally defined between upper and lower surfaces 76, 78 of the bridge region 38, while the width is generally measured perpendicular to the upper and lower surfaces 76, 78, as best shown in FIGS. 7 and 8a-c. The height of the bridge section may or may not correspond to the height of the plate in the cutter depending on the orientation of the cutter on the bridge section. In this manner, the width of the bridge region 38 is generally measured perpendicular to the height of the region 38. Generally speaking, for a constant cross-sectional area or for a given tensile load carried by the bridge section, as the width of the bridge region 38 is increased, the height of the bridge region 38 is decreased. For a given cross-sectional area, as the cutting aspect ratio increases (H/W), the force required to sever the bridge section is reduced.

Because the cut force is directly attributable to the size, shape, and aspect ratio of the cross-section of the bridge region 38, an Aspect Ratio Factor (ARF) is calculated for use in determining a desirable aspect ratio (i.e., height and width) of a bridge region 38. The ARF is determined by dividing the cut force in a tested orientation of a bridge portion by an average of the cut forces measured in both directions. As previously discussed, the aspect ratio of the bridge region 38 is defined as the height of the bridge region 38 in a cutter 72 divided by the width of the bridge region 38 in a cutter 72. Therefore, a given bridge region 38 having an aspect ratio of A would have an aspect ratio of 1/A when rotated 90 degrees in the cutter 72. Therefore, the ARF may be determined by the following equations for each aspect ratio:

$$ARF_A = \text{Cut Force}_A / ((\text{Cut Force}_A + \text{Cut Force}_{1/A})/2)$$

$$ARF_{1/A} = \text{Cut Force}_{1/A} / ((\text{Cut Force}_A + \text{Cut Force}_{1/A})/2)$$

For example, a force required to cut a square cross-section will be the same regardless of the orientation of the section in the cutter 72 as the width of the section is generally equal to the height. For a plate of the same cross-sectional area, but with an aspect ratio of 2 (i.e., the bridge region 38 is twice as wide as it is high), the cut force required to sever the bridge is reduced.

For example, the natural log of the aspect ratio for a plate having an aspect ratio of 2 is 0.69. From a regression of experimental data relating the aspect ratio to the ARF for cross sections made from Grade IV titanium, the natural logarithm of the ARF corresponding to the aspect ratio of 2 is approximately −0.1, which corresponds to an ARF of 0.904. Substituting the ARF value into the above $ARF_A$ equation and solving for Cut Force$_A$ yields a cut force that is roughly 83% of the load required to cut the same cross-section having an aspect ratio of 1/2. The cross-section having an aspect ratio of 1/2 has the same cross-sectional area as the section having an aspect ratio of 2, but the section having an aspect ratio of 1/2 is rotated 90 degrees in the cutting tool 72 (such that the above equation is solved for Cut Force$_{1/A}$ and the aspect ratio is 1/A), and is thus more difficult to cut.

Therefore, a bridge region 38 having an aspect ratio of 2 (i.e., the bridge region 38 is twice as wide as it is high) is easier to cut than a bridge portion having an aspect ratio of 1/2 (i.e., the bridge region 38 is twice as high as it is wide). It should be noted that when the bridge region 38 has an aspect ratio of either 2 or 1/2, that the bridge region 38 will have an identical cross-sectional area. In other words, the relationship between the width and height remains the same. For example, a plate 28 having a bridge region 38 measuring 2 mm in one direction and 1 mm in the other direction will yield a cross-sectional area of 2 mm$^2$. The aspect ratio only changes from 2 to 1/2 when the plate 28 is rotated 90 degrees in the cutting tool 72. When the bridge region 38 is cut along the 2 mm surface, the aspect ratio is 2 and the plate 28 is easily severed. Conversely, when the plate 28 is cut along the 1 mm section, the aspect ratio is 1/2 and the plate 28 requires a higher cut force in order to sever the bridge region 38. Therefore, cut force and aspect ratio are directly related.

Based on the inventors' research with a particular cutter, a cut force (i.e., applied to the handles of a cutter) with a particular cutter of 55.1 lbf is generally considered an acceptable force, allowing most surgeons to easily sever a plate 28 using cutting tools 72 commonly found in a crash cart of an emergency room. As previously discussed, the force required to cut or sever a given bridge region 38 of a plate 28 is, in part, dependent on the aspect ratio of the bridge region 38 to be cut. The plate 28 can be easily cut without reducing the cross-sectional area of the bridge region 38 beyond an acceptable limit by optimizing the aspect ratio of the bridge region's cross-section.

Typically, most devices used in sternal closure procedures are designed to withstand loads ranging from 400 N (90 lbf) to 1200 N (270 lbf). Such loads are generally applied by the patient during breathing, coughing, etc. and must be safely transmitted by one or more plates 28 to halves A, B via bridge fixation regions 36 and one or more bridge regions 38. Therefore, the first step in designing a plate 28 is to ensure that the bridge region 38 is large enough to carry such loads with an appropriate factor of safety. Once an adequate cross-sectional area is determined, the aspect ratio of the section is adjusted to facilitate severability of the section when quick removal of the plate 28 is required.

Figure 18:
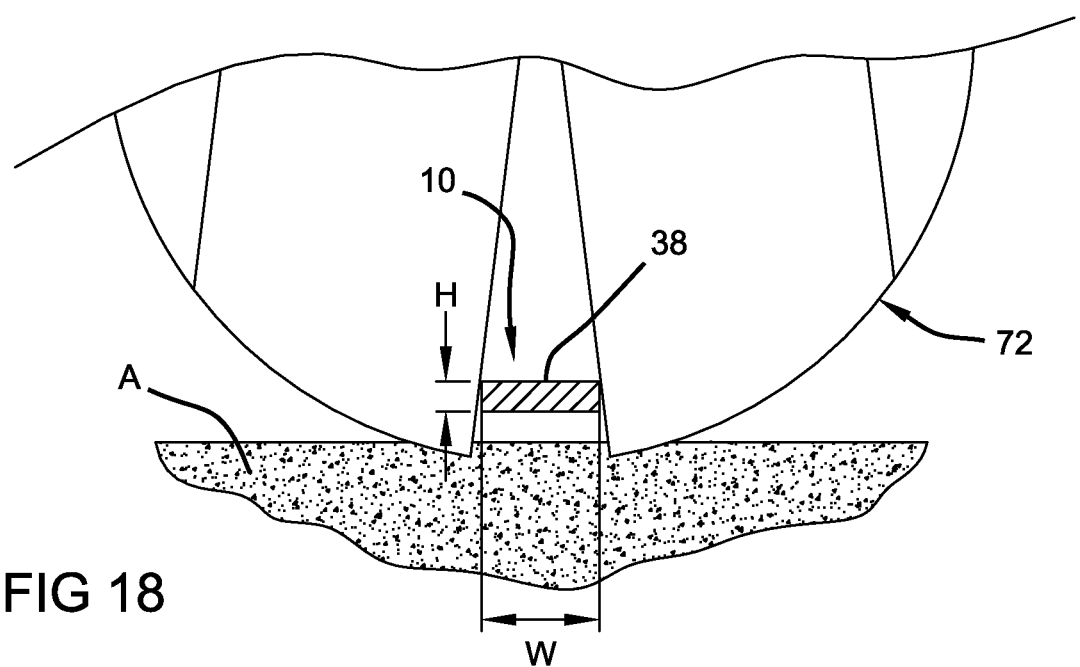
FIG. 18 is a perspective view of the plate of FIG. 7 with a bridge region of the plate engaged by another plate cutter, wire cutter, or pair of surgical scissors.
Figure 19:
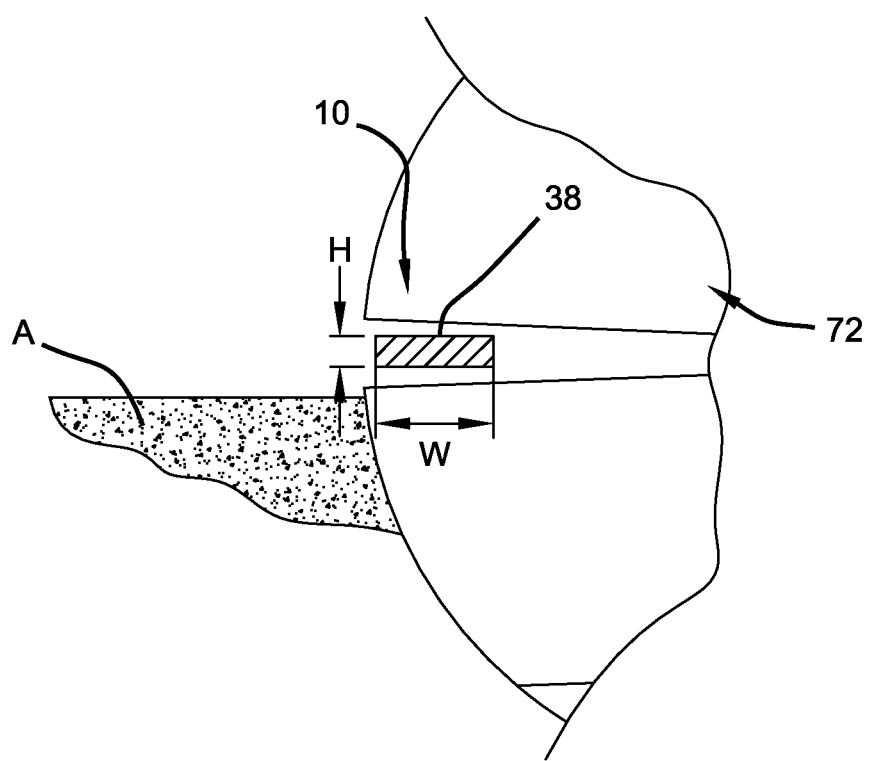
FIG. 19 is a perspective view of the plate of FIG. 7 with a bridge region of the plate engaged by another plate cutter, wire cutter, or pair of surgical scissors.

In adjusting the aspect ratio (i.e., height and width) of the bridge region 38, the following equations (A-H) are useful in determining the maximum cut height for a given bridge region 38, where $h_{max}$ is the maximum height of the bridge region 38, w is the width of the bridge region 38, and a is the area of the cross-section of the bridge region 38. It should be noted that while the following equations apply for any orientation of the plate 28 in the cutter 72, the use of the bridge width and maximum bridge section height is dependent on relating it to the cutting orientation as shown in FIG. 18. More generally, the height could be considered the height of the bridge region in the cutter 72 (and likewise the width of the bridge region in the cutter) and then the specific orientation of cutting drops out:

$$63.7 = ((1.30 \times 10^4)(a) + 8.76)\left(\frac{w}{h_{max}}\right)^{-0.140} \quad \text{A.}$$

$$55.1 = ((1.30 \times 10^4)(a) + 8.76)\left(\frac{w}{h_{max}}\right)^{-0.140} \quad \text{B.}$$

$$22.2 = ((1.30 \times 10^4)(a) + 8.76)\left(\frac{w}{h_{max}}\right)^{-0.140} \quad \text{C.}$$

$$19.2 = ((1.30 \times 10^4)(a) + 8.76)\left(\frac{w}{h_{max}}\right)^{-0.140} \quad \text{D.}$$

$$63.7 = ((1.224 \times 10^4)(a) + 3.68)\left(\frac{w}{h_{max}}\right)^{-0.124} \quad \text{E.}$$

$$55.1 = ((1.224 \times 10^4)(a) + 3.68)\left(\frac{w}{h_{max}}\right)^{-0.124} \quad \text{F.}$$

$$22.2 = ((1.224 \times 10^4)(a) + 3.68)\left(\frac{w}{h_{max}}\right)^{-0.124} \quad \text{G.}$$

$$19.2 = ((1.224 \times 10^4)(a) + 3.68)\left(\frac{w}{h_{max}}\right)^{-0.124} \quad \text{H.}$$

The constants on the left-hand side of the equations A-H (i.e., 63.7, 55.1, 22.2, and 19.2) refer to experimentally determined acceptable cut force values for a given bridge region 38. The following equation may be used to determine an acceptable cut force where CF refers to a Maximum allowable cut force; S1 refers to a slope of a cut force vs. cross-sectional area (determined experimentally); S2 refers to a slope of Ln (ARF) vs. Ln (aspect ratio) (determined experimentally); and C1 refers to a Y-intercept of the cut force vs. cross-sectional area data (determined experimentally):

$$CF = ((S1)(a) + C1)\left(\frac{w}{h_{max}}\right)^{S2}$$

For the actual cut force to be less than or equal to the maximum allowable cut force given a defined width w, the height H must be less than or equal to Hmax. For a rectangular cross section a=h*w the equation becomes:

$$CF = ((S1)(w)(h_{max}) + C1)\left(\frac{w}{h_{max}}\right)^{S2}$$

The cut force (applied to the handle of an instrument by a doctor or physician) requirements are 63.7 lbf, 55.1 lbf, 22.2 lbf, and 19.2 lbf, respectively, and generally provide a scale on which a plate designer may choose to set the cut force. The 63.7 lbf and 55.1 lbf cut force refer to the largest clinically relevant cutter. The 22.2 lbf and 19.2 lbf cut force refer to the smallest clinically relevant cutter. The constants S1, C1 and S2 are dependent on the material chosen. The cut force is initially determined for the largest relevant cutter. However, the following equation can be scaled using the experimentally determined ratio (L1 over L2) of cut force required to sever a given section using a first cutter (L1) versus experimentally determined cut force required to sever the same given section using a second cutter (L2). In this manner, the plate can be severed by other clinically relevant cutters, (e.g., the small cutter) with the scaled equation describing the required cut force is given as:

$$CF\left(\frac{CF_1}{CF_2}\right) = ((S1)(a) + C1)\left(\frac{w}{h_{max}}\right)^{S2}$$

Using several plate shape sections to determine L1/L2 and regressing the data, the appropriate relationship was experimentally determined to determine the 22.2 lbf and 19.2 lbf on the left hand side of the equation for the small clinically relevant cutter. In essence, this modification to the equation shows that a smaller cutter with the same hand force on the cutter requires a section that can be cut more easily.

While technically, it most correct to multiply S1 and C1 each by the ratio of cut force using the small cutter over cut force using the large cutter, the above equation is equivalent to dividing CF by the quantity (cut force using small cutter over cut force using the large cutter). This is how the equations A and B were scaled to obtain the equations C and D and how the equations E and F were scaled to obtain the equations G and H.

For example, equations A and E are both set to yield a cut force of 63.7 lbf with the area, width, and height as variables. Using this maximum cut force, for a rectangular section and using Grade 4 titanium with the largest clinically relevant cutter, equation A gives the relationship between height and width of the bridge section. If the maximum cut height (which may be the same as the width of the bridge section, as shown in FIG. 18) is set at 0.05 inches, the maximum height of the bridge will be determined to be 0.0784 inches. From the assigned width and determined height, the cross-sectional area can be determined to be 0.00392 square inches. Any height of the bridge less than 0.0784 inches will allow for cutting at a cut force.

In contrast, using the same equation A based on the same maximum cut force, a rectangular section, and the same cutter, if the height of the plate in the cutter (Corresponding to the width of the bridge section in proposed FIG. 18A) were set at 0.0784 inches (equivalent to the maximum bridge height of the bridge section determined in the prior example), then the maximum height of the bridge section would be determined to be 0.0567 inches. From the set width and the determined height, the cross-sectional area can be determined to be 0.00445 square inches. For the same cut force, the geometry determined in the second example has a cross-sectional area 13.4% larger than the geometry of the first example. This directly translates into the ability of the bridge section of example 2 to transmit a tensile load 13.4% higher than the bridge section of example 1. In this manner, if a plate must withstand a specified load, and the cross-sectional area needed to withstand the load is known, the aspect ratio can be adjusted using equations A-H to optimize the plate design (i.e., height and width) for both strength and severability. The following table summarizes examples 1 and 2:

|  | Example 1 | Example 2 |
|---|---|---|
| Maximum Cut Force | 63.7 | 63.7 |
| Set Width | 0.05 | 0.0784 |
| Determined Height | 0.0784 | 0.0567 |
| Area of Cross Section | 0.00392 | 0.00445 |
| Section Shape | 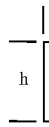 | 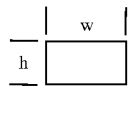 |

In the same way, the experimentally measured force on the handle can be translated to the actual force seen by the plate using the mechanical advantage of the given cutter. For the double action cutter used as the largest clinically relevant cutter, the mechanical advantage was determined to be 6.1 to 7.1 depending on hand position, with the plate positioned so that up to 2 mm of cutter extended beyond the plate. In the tested position, the mechanical advantage was determined to be 6.8. From this, the actual force seen by the plate associated with an applied cut force of 63.7 lbf can be determined in the range of 388 lbf to 452 lbf depending on user hand position, and 433 lbf in the test fixture position. The same determination could be made for the small cutter.

Based on this calculation, the cut force equation can be rewritten to describe the force applied to the plate ($P_{CF}$), using the mechanical advantage (MA) of the cutter:

$$P_{CF} = ((S1)(a) + C1)\left(\frac{w}{h_{max}}\right)^{S2}(MA)$$

Since $P_{CF}=(CF)(MA)$, it is readily apparent that this equation is equivalent to the previously described relationship. Using the maximum of the range of mechanical advantages measured for the large cutter, equations A, B, E, and F are can be rewritten as A', B', E' and F' as shown below.

$$452 = ((1.30 \times 10^4)(a) + 8.76)\left(\frac{w}{h_{max}}\right)^{-0.140}(7.1) \quad \text{A'.}$$

$$391 = ((1.30 \times 10^4)(a) + 8.76)\left(\frac{w}{h_{max}}\right)^{-0.140}(7.1) \quad \text{B'.}$$

$$452 = ((1.224 \times 10^4)(a) + 3.68)\left(\frac{w}{h_{max}}\right)^{-0.124}(7.1) \quad \text{E'.}$$

$$391 = ((1.224 \times 10^4)(a) + 3.68)\left(\frac{w}{h_{max}}\right)^{-0.124}(7.1) \quad \text{F'.}$$

By similar means, this principle could be applied to the small cutter tested or to any other relevant cutter to determine the maximum severing force seen by a given plate. This method could also be applied to model the cut force of materials other than Grade 2 or Grade 4 commercially pure titanium using the same characteristic equation and similar testing.

Figure 20:
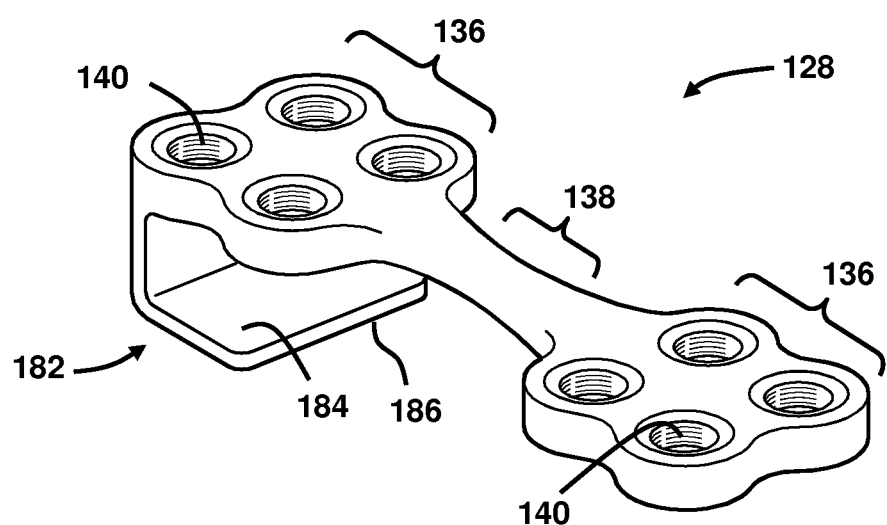
FIG. 20 is a perspective view of an elongated plate according to another embodiment of the present teachings having a hook.

Referring to FIG. 20, a plate 128 according to the teachings of an additional embodiment is shown. Plate 128 is generally similar to plate 28 and thus a detailed description of plate 128 is not necessary. However, unlike plate 28, plate 128 includes at least one hook 182. The hook 182 is an extension of the plate 128 and is located at the end of one or more of the bone fixation regions 136.

The hook 182 includes a bone contact surface 184 and an outer surface 186. The hook 182 first extends from the bone fixation region 136 at a right angle to the plate 128 for a distance slightly greater than the width of the sternum 16. The hook 182 then extends toward the bridge region 138 of the plate 128 in a direction parallel to the plate 128 so as to engage the bone laterally. As a result of this configuration, the hook 182 is able to encompass the external portion of severed portion A or B of sternum 16. Consequently, plate 128 is better able to grip the reapproximated halves A or B of sternum 16 and is consequently better able to secure the halves A and B together to prevent movement of the halves A and B. It must be noted that any of the bone fixation regions 36 of any of the other embodiments may be adapted to include hook 182.

The description of the teachings is merely exemplary in nature and, thus, variations that do not depart from the gist of the teachings are intended to be within the scope of the teachings. Such variations are not to be regarded as a departure from the spirit and scope of the teachings.

What is claimed is:
1. A method comprising:
   determining a load to be supported across separated bone regions by a bridge region of a bone plate;
   determining an acceptable cut force (CF) for the bridge region;
   determining a cross-sectional area (a) of the bridge region based on the determined load;
   determining a height (h) and a width (w) of the bridge region based on the following equation:

$$CF = ((S1)(a) + C1)\left(\frac{w}{h_{max}}\right)^{S2}$$

wherein "S1," "C1," and "S2" are constants for a given bridge material, constant "S1" is a slope of a curve defined by a range of cut force versus cross-sectional area, constant "C1" is a Y-intercept of the curve, and constant "S2" is a slope of Ln (ARF) versus Ln (aspect ratio), wherein "ARF" is an aspect ratio factor that is defined by:

$$ARF = \frac{CF1}{(CF1 + CF2)/2}$$

wherein ($h_{max}$) is a maximum height of the bridge region, "CF1" is a first cut force associated with one of the width (w) and the maximum height ($h_{max}$) of the bridge region, "CF2" is a second cut force associated with the other of the width (w) and the maximum height ($h_{max}$), and the aspect ratio is a ratio between the maximum height ($h_{max}$) and the width (w); and
  providing a bone plate including a bridge region having the height (h) and width (w) for securing the separated bone regions.

2. The method of claim 1, wherein said determined acceptable cut force (CF) is a maximum allowable cut force for the bridge region.

3. The method of claim 1, further comprising removing the bone plate from a sternum by severing the bridge region with a cutting tool.

4. The method of claim 3, wherein the severing includes cutting along the width (w).

5. The method of claim 3, further comprising securing the plate to the separated bone region, the plate including a first fixation region on a first end of the bridge region and a second fixation region on a second end of the bridge region, the securing including fixing the first fixation region to a first side of the separated bone region and fixing the second fixation region to a second side of the separated bone region.

6. The method of claim 5, wherein the first fixation region includes a hook and the securing includes locating the hook around the first side of the separated bone region.

7. The method of claim 1, further comprising securing the plate to a separated sternum, the plate including a first fixation region on a first end of the bridge region and a second fixation region on a second end of the bridge region, the securing including coupling the first fixation region to a first side of the separated sternum and coupling the second fixation region to a second side of the separated sternum.

8. The method of claim 7, wherein the first fixation region includes a hook and the securing includes locating the hook around the first side of the separated sternum.

9. The method of claim 1, wherein the cross-sectional area (a) is defined by the product of the maximum height ($h_{max}$) and the width (w).

10. The method of claim 1, wherein the determined height (h) is less than or equal to the maximum height ($h_{max}$).

11. The method of claim 1, wherein the first cut force (CF1) is defined along the width (w).

12. The method of claim 1, wherein the first cut force (CF1) is defined along the height (h).

13. A bone plate comprising:
  a first fixation region adapted to secure the bone plate to a first side of a separated bone region;
  a second fixation region adapted to secure the bone plate to a second side of the separated bone region; and
  a bridge region extending between and coupling said first and second fixation regions to one another, said bridge region defining a cross-sectional area (a) severable by a predetermined maximum allowable cut force (CF) and adapted to support a predetermined load across the separated bone region, said bridge region being defined by:

$$CF = ((S1)(a) + C1)\left(\frac{w}{h_{max}}\right)^{S2}$$

and having a width (w) and a height (h) that is less than or equal to a maximum height ($h_{max}$), wherein "S1," "C1," and "S2" are constants for a given bridge material, constant "S1" is a slope of a curve defined by a range of cut force versus cross-sectional area, constant "C1" is a Y-intercept of the curve, and constant "S2" being a slope of Ln (ARF) versus Ln (aspect ratio), and "ARF" is an aspect ratio factor that is defined by:

$$ARF = \frac{CF1}{(CF1 + CF2)/2}$$

wherein "CF1" is a first cut force associated with one of the width (w) and the maximum height ($h_{max}$) of said bridge region, "CF2" is a second cut force associated with the other of the width (w) and the maximum height ($h_{max}$), and the aspect ratio is a ratio between the maximum height ($h_{max}$) and the width (w).

14. The bone plate of claim 13, wherein said first fixation region includes a hook adapted to extend around the first side of a separated bone region.

15. The bone plate of claim 14, wherein said second fixation region includes a first aperture adapted to receive a first fastener to couple the bone plate to the second side of the separated bone region.

16. The bone plate of claim 15, wherein said first fixation region includes a second aperture located between said bridge region and said hook and adapted to receive a second fastener to couple the bone plate to the second side of the separated bone region.

17. The bone plate of claim 14, wherein said hook is adapted to extend around a first side of a separated sternum.

18. The bone plate of claim 13, wherein the cross-sectional area (a) is defined by the product of the maximum height ($h_{max}$) and the width (w).

19. The bone plate of claim 13, wherein the first cut force (CF1) is defined along the width (w).

20. The bone plate of claim 13, wherein the first cut force (CF1) is defined along the height (h).

* * * * *